(12) United States Patent
Avidov et al.

(10) Patent No.: US 11,426,434 B2
(45) Date of Patent: Aug. 30, 2022

(54) BEE-INGESTIBLE COMPOSITIONS, METHODS OF USING SAME FOR PRODUCING HONEY AND HONEY PRODUCED THEREBY

(71) Applicant: Phytopharma International Ltd., Afula (IL)

(72) Inventors: Amit Dov Avidov, Kiryat-Tivon (IL); Ilan Ben Simon, Kfar-Vradim (IL)

(73) Assignee: Phytopharma International Ltd., Afula (IL)

( * ) Notice: Subject to any disclaimer, the term of this patent is extended or adjusted under 35 U.S.C. 154(b) by 731 days.

(21) Appl. No.: 16/383,612

(22) Filed: Apr. 14, 2019

(65) Prior Publication Data

US 2019/0231826 A1     Aug. 1, 2019

Related U.S. Application Data

(60) Division of application No. 15/876,219, filed on Jan. 22, 2018, now Pat. No. 10,278,996, which is a continuation of application No. PCT/IL2016/050801, filed on Jul. 21, 2016.

(60) Provisional application No. 62/195,311, filed on Jul. 22, 2015.

(51) Int. Cl.

| | | |
|---|---|---|
| *A61K 35/644* | (2015.01) | |
| *A23K 20/158* | (2016.01) | |
| *A23K 20/163* | (2016.01) | |
| *A23K 50/90* | (2016.01) | |
| *A23L 21/25* | (2016.01) | |
| *A61P 21/00* | (2006.01) | |
| *A61P 27/06* | (2006.01) | |
| *A61P 25/28* | (2006.01) | |
| *A61P 25/30* | (2006.01) | |
| *A61P 11/06* | (2006.01) | |
| *A61P 25/32* | (2006.01) | |
| *A61P 19/02* | (2006.01) | |
| *A61P 25/04* | (2006.01) | |
| *A61P 25/18* | (2006.01) | |
| *A61P 25/24* | (2006.01) | |
| *A61P 25/08* | (2006.01) | |
| *A61P 29/00* | (2006.01) | |
| *A61P 1/08* | (2006.01) | |
| *A61P 25/06* | (2006.01) | |
| *A61K 9/00* | (2006.01) | |
| *A61K 31/05* | (2006.01) | |
| *A61K 31/352* | (2006.01) | |
| *A61K 36/185* | (2006.01) | |

(52) U.S. Cl.
CPC .......... *A61K 35/644* (2013.01); *A23K 20/158* (2016.05); *A23K 20/163* (2016.05); *A23K 50/90* (2016.05); *A23L 21/25* (2016.08); *A61K 9/0056* (2013.01); *A61K 31/05* (2013.01); *A61K 31/352* (2013.01); *A61K 36/185* (2013.01); *A61P 1/08* (2018.01); *A61P 11/06* (2018.01); *A61P 19/02* (2018.01); *A61P 21/00* (2018.01); *A61P 25/04* (2018.01); *A61P 25/06* (2018.01); *A61P 25/08* (2018.01); *A61P 25/18* (2018.01); *A61P 25/24* (2018.01); *A61P 25/28* (2018.01); *A61P 25/30* (2018.01); *A61P 25/32* (2018.01); *A61P 27/06* (2018.01); *A61P 29/00* (2018.01); *A23V 2002/00* (2013.01)

(58) Field of Classification Search
None
See application file for complete search history.

(56) References Cited

U.S. PATENT DOCUMENTS

| | | |
|---|---|---|
| 5,612,074 A | 3/1997 | Leach |
| 5,711,953 A | 1/1998 | Bassett |
| 8,445,034 B1 | 5/2013 | Coles, Jr. |
| 8,962,584 B2 | 2/2015 | Sela et al. |
| 2004/0138293 A1 | 7/2004 | Werner et al. |
| 2013/0089600 A1 | 4/2013 | Winnicki |
| 2014/0302086 A1 | 10/2014 | Kelly |
| 2018/0140644 A1 | 5/2018 | Avidov et al. |
| 2018/0318361 A1 | 11/2018 | Eyal |

FOREIGN PATENT DOCUMENTS

| | | |
|---|---|---|
| CL | 201402751 | 10/2014 |
| CL | 201503546 | 12/2015 |
| CN | 1547479 | 11/2004 |
| CN | 1885117 | 12/2006 |
| CN | 101467598 | 7/2009 |
| CN | 101678059 | 3/2010 |
| CN | 101869235 | 10/2010 |
| CN | 101932314 | 12/2010 |
| CN | 102083430 | 6/2011 |
| CN | 104256243 | 1/2015 |
| CN | 104302193 | 1/2015 |
| CN | 104381774 | 3/2015 |
| CN | 101977596 | 2/2016 |

(Continued)

OTHER PUBLICATIONS

Marijuana MarketTM, Edibles & Drinks Menu, retrieved from Internet Archive: https://web.archive.org/web/20150101225405/ http://www.marijuanamarket.com/marijuanaedibles.html. (Year: 2015).*

(Continued)

*Primary Examiner* — Michael Barker

(57) ABSTRACT

A bee ingestible composition comprising a bee food base and THC and/or CBD is provided. Also provided are methods of producing honey, honey obtainable by these methods and uses of same.

1 Claim, 9 Drawing Sheets

(56) References Cited

FOREIGN PATENT DOCUMENTS

| | | |
|---|---|---|
| CN | 105505565 | 4/2016 |
| CN | 105764504 | 7/2016 |
| GB | 156041 | 1/1921 |
| GR | 20160200212 | 3/2018 |
| JP | 61-265056 | 11/1986 |
| JP | 11-169098 | 6/1999 |
| JP | 2000-333619 | 12/2000 |
| JP | 2004-529892 | 9/2004 |
| JP | 2008-208036 | 9/2008 |
| KR | 1990-0004266 | 4/1990 |
| WO | WO 2006/080019 | 8/2006 |
| WO | WO 2015/020516 | 2/2015 |
| WO | WO 2017/013661 | 1/2017 |
| WO | WO 2017/072704 | 5/2017 |
| WO | WO 2017/093986 | 6/2017 |

OTHER PUBLICATIONS cannahoney.com/index.html, retrieved Apr. 20, 2022 (Year: 2022).*
Examination Report dated May 20, 2019 From the Republica de Colombia, Superintendencia de Industria y Comercio, Gobierno de Columbia Re. Application No. NC2018/0001115 and Its Translation Into English. (9 Pages).
Translation Dated Feb. 4, 2022 of Decision of Rejection dated Jan. 18, 2022 From the Korean Intellectual Property Office Re. Application No. 10-2018-7005317. (7 Pages).
Communication Pursuant to Article 94(3) EPC dated Jul. 20, 2020 From the European Patent Office Re. Application No. 16753708.3. (4 Pages).
Communication Pursuant to Article 94(3) EPC dated Dec. 4, 2020 From the European Patent Office Re. Application No. 16753708.3. (4 Pages).
Grounds of Reason of Rejection dated Feb. 24, 2022 From the Korean Intellectual Property Office Re. Application No. 2018-7005317 and Its Translation Into English. (5 Pages).
Search Report and Opinion dated Dec. 18, 2019 From the Servico Publico Federal, Ministerio da Economia, Instituto National da Propriedade Industrial do Brasil Re. Application No. BR112018001310-2 and Its Translation Into English. (6 Pages).
Search Report and Written Opinion dated Jan. 15, 2020 From the INAPI, Ministerio de Economia, Fomento y Turismo, Gobierno de Chile Re. Application No. 201800162 and Its Translation Into English. (16 Pages).
Fitzcharles et al. "Comparison of Canadian and Israeli Rheumatologists' Understanding of Cannabinoid Use as a Therapy for Rheumatic Diseases", EULAR 2014, Annals of the Rheumatic Diseases, Scientific Abstracts, 73(Suppl.2): 1177, # AB1133, Jun. 1, 2014.
Ground(s) of Reason of Rejection dated Oct. 14, 2021 From the Korean Intellectual Property Office Re. Application No. 2018-7005317. (9 Pages).
Communication Pursuant to Article 94(3) EPC dated Apr. 10, 2019 From the European Patent Office Re. Application No. 16753708.3. (4 Pages).
Communication Pursuant to Article 94(30 EPC dated Aug. 29, 2018 From the European Patent Office Re. Application No. 16753708.3. (6 Pages).
Examination Report dated Feb. 11, 2019 From the Republica de Colombia, Superintendencia de Industria y Comercio, Gobierno de Columbia Re. Application No. NC2018/0001115 and its Translation Into English. (14 Pages).
Examination Report dated Feb. 13, 2018 From the Republica de Colombia, Superintendencia de Industria y Comercio, Gobierno de Columbia Re. Application No. NC2018/0001115 and its Translation Into English. (4 Pages).
International Preliminary Report on Patentability dated Feb. 1, 2018 From the International Bureau of WIPO Re. Application No. PCT/IL2016/050801. (7 Pages).
International Search Report and the Written Opinion dated Oct. 20, 2016 From the International Searching Authority Re. Application No. PCT/IL2016/050801.
Notice of Allowance dated Feb. 25, 2019 From the US Patent and Trademark Office Re. U.S. Appl. No. 15/876,219. (18 pages).
Official Action dated Sep. 5, 2018 From the US Patent and Trademark Office Re. U.S. Appl. No. 15/876,219. (14 pages).
Requisition by the Examiner dated Sep. 5, 2018 From the Innovation, Science and Economic Development Canada, Canadian Intellectual Property Office Re. Application No. 2,993,023. (5 Pages).
Requisition by the Examiner dated Jan. 22, 2019 From the Innovation, Science and Economic Development Canada, Canadian Intellectual Property Office Re. Application No. 2,993,023. (4 Pages).
Requisition by the Examiner dated Mar. 29, 2018 From the Innovation, Science and Economic Development Canada, Canadian Intellectual Property Office Re. Application No. 2,993,023. (5 Pages).
Restriction Official Action dated Jun. 22, 2018 From the US Patent and Trademark Office Re. U.S. Appl. No. 15/876,219. (6 pages).
Aboulaich et al. "Variations and Origin of the Atmospheric Pollen of Cannabis Detected in the Province of Tetouan (NW Marocco): 2008-2010", Science of Total Environment, XP055501632, 443: 413-419, Available Online Nov. 30, 2012.
Aggarwal et al. "From 32 Ounces to Zero: A Medical Geographic Study of Dispensing a Cultivated Batch of 'Plum' Cannabis Flowers to Medical Marijuana Patients in Washington State", Journal of Psychoactive Drugs, 45(2): 141-155, Apr.-Jun. 2013.
Anonymus "Hemp Honey—Frequently Asked Questions: About Hemp Honey Liquid", Retrieved From the Internet, 1 P., Aug. 4, 2014.
Bibi et al. "Pollen Analysis and Heavy Metals Detection in Honev Samples From Seven Selected Countries", Pakistan Journal of Botany, XP002762572, 40(2): 507-516, Apr. 2008.
Bulletin Solutions "Cannabis and Bees", vBulletin Solutions, Version 4.2.0, 4 P., 2015.
Dalio "Cannabis *sativa*—An Important Subsistence Pollen Source for Apis Mellifera", IOSR Journal of Pharmacy and Biological Sciences, 1(4): 1-3, Jul.-Aug. 2012.
Dalio "Cannabis *sativa*—An Important Subsistence Pollen Source for Apis Mellifera", Journal of Pharmacy and Biological Sciences, 1(4): 01-03, Jul.-Aug. 2012.
Diez et al. "Physicochemical Parameters and Pollen Analysis of Moroccan Honeydew Honeys", International Journal of Food Science and Technology, XP002762571, 39(2): 167-176, Feb. 2004. p. 167, col. 1, Table 2, p. 170.
Garg "Palynocontents of Bee-Collected Pollen Loads of Autumn Season in Bhimal, India.", Taiwania; 41(3): 197-207, 1996.
Kershner "New Insights on Marijuana in Israel, Where It's Illegal. Studying Marijuana and Its Loftier Purpose", The New York Times, p. 1-3, Jan. 1, 2013.
Khan et al. "Study of Physiochemical Characteristics and Pollen Spectrum of Honey available in Lahore", Pakistan Journal of Biochem. Mol. Biol. 42(2): 58-62, 2009.
Lamont "Honeybees and Hemp: Where Did We Go Wrong?", Smokey Mountain News, 2 P., Apr. 4, 2007.
Paris et al. "The Constituents of Cannabis *sativa* Pollen", Economic Botany, 29(3): 245-253, Jul.-Sep. 1975.
Ross et al. "Flavonoid Glycosides and Cannabinoids from the Pollen of Cannabis *sativa* L.", Phytochemical Analysis, 16: 45-48 2005.
Terrab et al. "Study of Plants Visited by Honeybees (Apis *mellifera* L.) in the Central Rif Region (N. Marocco) Using Pollen Analysis", Grana, XP055501672, 44(3): 209-215, Sep. 2005.
Weirich et al. "Antioxidant Enzymes in the Honey Bee, Apis Mellifera", Apidologie, 33(1): 3-14, Jan. 2002.
Search Report and Written Opinion dated Apr. 9, 2019 From the INAPI, Ministerio de Economia, Fomento y Turismo, Gobierno de Chile Re. Application No. 201800162 and Its Translation Into English. (16 Pages).
Seshata "El Cannabis Frente al Problema de Colapso de las Colonias", Sensi Seeds, 14 P., Jul. 9, 2015.

(56) References Cited

OTHER PUBLICATIONS

Translation Dated Nov. 9, 2021 of Ground(s) of Reason of Rejection dated Oct. 14, 2021 From the Korean Intellectual Property Office Re. Application No. 2018-7005317. (9 Pages).
Examination Report dated Dec. 2, 2019 From the Australian Government, IP Australia Re. Application No. 2016295728. (3 Pages).
Notice of Reasons for Rejection dated Sep. 29, 2020 From the Japan Patent Office Re. Application No. 2018-522896 and Its Translation Into English.
Notification of Office Action and Search Report dated May 11, 2020 From the State Intellectual Property Office of the People's Republic of China Re. Application No. 201680045209.7. (12 Pages).
Translation Dated May 31, 2020 of Notification of Office Action dated May 11, 2020 From the State Intellectual Property Office of the People's Republic of China Re. Application No. 201680045209.7. (7 Pages).
Ground(s) of Reason of Rejection dated Jan. 18, 2022 From the Korean Intellectual Property Office Re. Application No. 10-2018-7005317. (6 Pages).
Notification of Office Action and Search Report dated Dec. 7, 2020 From the State Intellectual Property Office of the People's Republic of China Re. Application No. 201680045209.7 and Its Translation of Office Action Into English. (5 Pages).
Requisition by the Examiner dated Jun. 20, 2019 From the Innovation, Science and Economic Development Canada, Canadian Intellectual Property Office Re. Application No. 2,993,023. (6 Pages).
BudBuddy "Honey Jars Small 50 ML1", Retrieved from the Internet, 3 P., Jun. 27, 2019.
Smith "Cannabis-Infused Honey: A Must Have Natural Medicine", Cannabis Now, 1 P., Retrieved from Internet Jun. 27, 2019.
Notice of Reason(s) for Rejection dated Jun. 8, 2021 From the Japan Patent Office Re. Application No. 2018-522896 and Its Translation Into English. (6 Pages).
Examination Report Under Sections 12 & 13 of the Patents Act, 1970 and the Patents Rules, 2003 dated May 17, 2021 From the Government of India, Intellectual Property India, Patents, Designs, Trade Marks, Geographical Indications, The Patent Office Re. Application No. 201827002723. (6 Pages).
Office Action dated Oct. 25, 2020 From the Israel Patent Office Re. Application No. 257078 and Its Translation Into English. (7 Pages).
Hearing Notice Under Sections 12 & 13 of the Patents Act, 1970 and the Patents Rules, 2003 dated Oct. 27, 2021 From the Government of India, Intellectual Property India, Patents, Designs, Trade Marks, Geographical Indications, The Patent Office Re. Application No. 201827002723.(3 Pages).

\* cited by examiner

BEE-INGESTIBLE COMPOSITIONS, METHODS OF USING SAME FOR PRODUCING HONEY AND HONEY PRODUCED THEREBY

RELATED APPLICATIONS

This application is a division of U.S. patent application Ser. No. 15/876,219 filed on Jan. 22, 2018 which is a continuation of PCT Patent Application No. PCT/IL2016/050801, having International Filing Date of Jul. 21, 2016, which claims the benefit of priority under 35 USC § 119(e) of U.S. Provisional Patent Application No. 62/195,311 filed on Jul. 22, 2015, the contents of which are incorporated herein by reference in their entirety.

FIELD AND BACKGROUND OF THE INVENTION

The present invention, in some embodiments thereof, relates to bee-ingestible compositions, methods of using same for producing honey and honey produced thereby.

*Cannabis*, more commonly known as marijuana, is a genus of flowering plants that includes at least three species, *Cannabis sativa, Cannabis indica,* and *Cannabis ruderalis* as determined by plant phenotypes and secondary metabolite profiles.

The use of *cannabis* for social and medical purposes has been known for almost of all humanity's recorded history. *Cannabis* is most commonly administered via inhalation or consumption of marijuana-infused food and drink.

Several medicinal uses have been found for the active ingredients of *cannabis*, including the ingredients tetrahydrocannabinol (THC), cannabinol (CBN), cannabidiol (CBD) and cannabichromene (CBC). The medicinal uses of *cannabis* include treatment of nausea and pain associated with cancer and chemotherapy; nausea, pain and wasting associated with AIDS; arthritis and rheumatism; glaucoma; migraines; muscle spasticity associated with multiple sclerosis and paralysis; alcohol and narcotics withdrawal; stress and depression; asthma; and epileptic seizures.

Despite the many proven or suspected benefits of *cannabis*, legal and social barriers prevent its widespread use.

There presently exists a need to provide more effective and safer *cannabis* extracts for various medical uses.

Honey has been used as a natural remedy and therapeutic aid since ancient times. The anti-microbial properties of honey have long formed part of both folk and scientific knowledge. Recently it has been suggested that the process of production of nectar into honey, naturally intensifies the effect of active ingredients present in the nectar, making them more effective and readily absorbed by the body. Products based on this scientific finding include LifeMel Honey, the world's most expensive honey and also disclosed in WO 2006/080019.

Additional background art includes:

U.S. Pat. No. 8,445,034 teaches systems and methods for fabricating a medicine by preparing a *cannabis* plant material and classifying the *cannabis* plant material into an acid, neutral, or analog form; extracting cannabinoids from the *cannabis* plant material by either a reflux process through evaporating and condensing the *cannabis* plant material or an ultrasonic extraction process of the *cannabis* plant material with ultrasonic waves; and infusing the cannabinoids with glycerine or honey to produce the medicine from a *cannabis* plant;

www(dot)thctalk(dot)com/*cannabis*-forum/archive/index(dot)php/t-82646(dot)html.

SUMMARY OF THE INVENTION

According to an aspect of some embodiments of the present invention there is provided a bee ingestible composition comprising a bee food base and THC and/or CBD.

According to some embodiments of the invention, the bee ingestible composition comprises *cannabis* oil.

According to some embodiments of the invention, the bee ingestible composition further comprises oil for rendering the composition more fluid.

According to some embodiments of the invention, said oil comprises an olive oil.

According to some embodiments of the invention, said bee food base is in a solid form.

According to some embodiments of the invention, said bee food base is in a liquid form.

According to some embodiments of the invention, said bee food base is in a semi-solid form.

According to some embodiments of the invention, the bee ingestible composition is a paste.

According to some embodiments of the invention, said bee food base comprises a natural bee feed.

According to some embodiments of the invention, said bee food base comprises a non-natural bee feed.

According to some embodiments of the invention, said bee food base is selected from the group consisting of honey, pollen, nectar, a carbohydrate solution and mixtures thereof.

According to some embodiments of the invention, said bee food base is selected from the group consisting of wheat, soybean flour, yeast, corn syrup, beet sugar syrup, isomerized corn syrup and type-50 sugar syrup.

According to some embodiments of the invention, said bee food base is honey.

According to some embodiments of the invention, said *cannabis* oil comprises said THC and/or CBD.

According to some embodiments of the invention, the bee-ingestible composition further comprises a pharmaceutical selected from the group consisting of an anti-allergic agent, an anti-inflammatory agent, an antioxidant, an anti-microbial agent, an antibacterial agent, an antifungal agent, an antiviral agent, an anti-cancer agent, an apoptosis inducing agent and an anti-diarrheal agent.

According to some embodiments of the invention, said pharmaceutical is a plant-derived pharmaceutical.

According to some embodiments of the invention, said pharmaceutical is not naturally present in *cannabis* trichome or *cannabis* oil.

According to some embodiments of the invention, said pharmaceutical is selected from the group consisting of a flavanoid, a heteroside, a polyphenol and a terpenoid.

According to some embodiments of the invention, said flavanoid is naringin.

According to some embodiments of the invention, said bee food base is present in the bee-ingestible composition at an amount of at least 50%.

According to some embodiments of the invention, said CBD and/or THC in said *cannabis* oil is present in the bee-ingestible composition at an amount not exceeding 1%.

According to some embodiments of the invention, the bee-ingestible composition comprised:
50-99.9% bee food base;
0.1-5% *cannabis* oil; and optionally
0.1-1% pharmaceutical.

According to an aspect of some embodiments of the present invention there is provided a method of producing honey comprising:
(a) feeding bees with the bee ingestible composition; and
(b) collecting the honey produced by said bees.

According to an aspect of some embodiments of the present invention there is provided honey obtainable according to the method described herein.

According to some embodiments of the invention, the honey is substantially free of plant material.

According to an aspect of some embodiments of the present invention there is provided honey comprising THC and/or CBD and a pharmaceutical which is not-naturally present in *cannabis*.

According to some embodiments of the invention, said pharmaceutical comprises a plant derived pharmaceutical.

According to some embodiments of the invention, the honey is characterized in that it comprises about 1,000 or more fold lower (e.g., about 10,000 fold lower) concentration of THC and/or CBD than that present in the *cannabis* oil used to prepare said bee-ingestible composition, and optionally about 4 or more fold lower concentration of THC and/or CBD than the bee-ingestible composition itself.

According to an aspect of some embodiments of the present invention there is provided honey comprising 5 ppm-500 ppm THC and/or CBD.

According to an aspect of some embodiments of the present invention there is provided honey comprising 5 ppm-400 ppm THC and/or CBD.

According to an aspect of some embodiments of the present invention there is provided honey comprising 5 ppm-300 ppm THC and/or CBD.

According to an aspect of some embodiments of the present invention there is provided honey comprising 10 ppm-200 ppm THC and/or CBD.

According to some embodiments of the invention, the honey comprises 50 ppm-100 ppm THC and/or CBD.

According to some embodiments of the invention, the honey comprises 50 ppm-80 ppm THC and/or CBD.

According to some embodiments of the invention, the honey further comprises a pharmaceutical.

According to some embodiments of the invention, the honey is in a in a semi-solid form.

According to some embodiments of the invention, the honey is in a solid form.

According to some embodiments of the invention, the honey is in a liquid form.

According to an aspect of some embodiments of the present invention there is provided a processed product comprising the honey described herein.

According to an aspect of some embodiments of the present invention there is provided a method of treating a medical condition which is alleviated by *cannabis*, the method comprising administering to a subject in need thereof a therapeutically effective amount of the honey or a processed product thereof, thereby treating the medical condition which is alleviated by *cannabis*.

According to some embodiments of the invention, said medical condition is selected from the group consisting of nausea and pain associated with cancer and chemotherapy; nausea, pain and wasting associated with AIDS; arthritis and rheumatism; glaucoma; migraine; muscle spasticity associated with multiple sclerosis and paralysis; alcohol and narcotics withdrawal; stress; depression; asthma; epileptic seizures, dementia, fibromyalgia, and post-traumatic stress disorder (PTSD).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
FIG. 1 is a photograph showing the attraction of honey bees to the various feeding protocols. Attraction levels 1 and 9 are exemplified.
Figure 2:
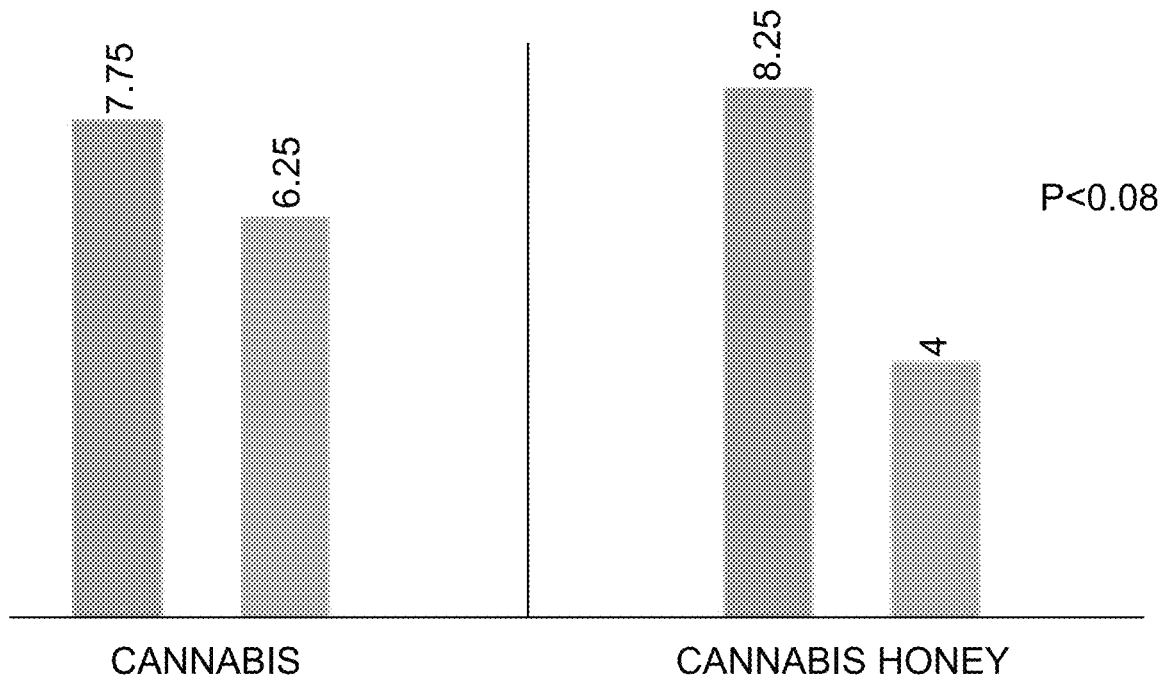
FIG. 2 is a graph showing changes in strongest pain during 24 hours in fibromyalgia patients, t-test showing statistical trend in *cannabis* honey group. Orange bars: average of questioner #I and average of questioner #III. Grey bars: average of questioner #II and average of questioner #IV.
Figure 3:
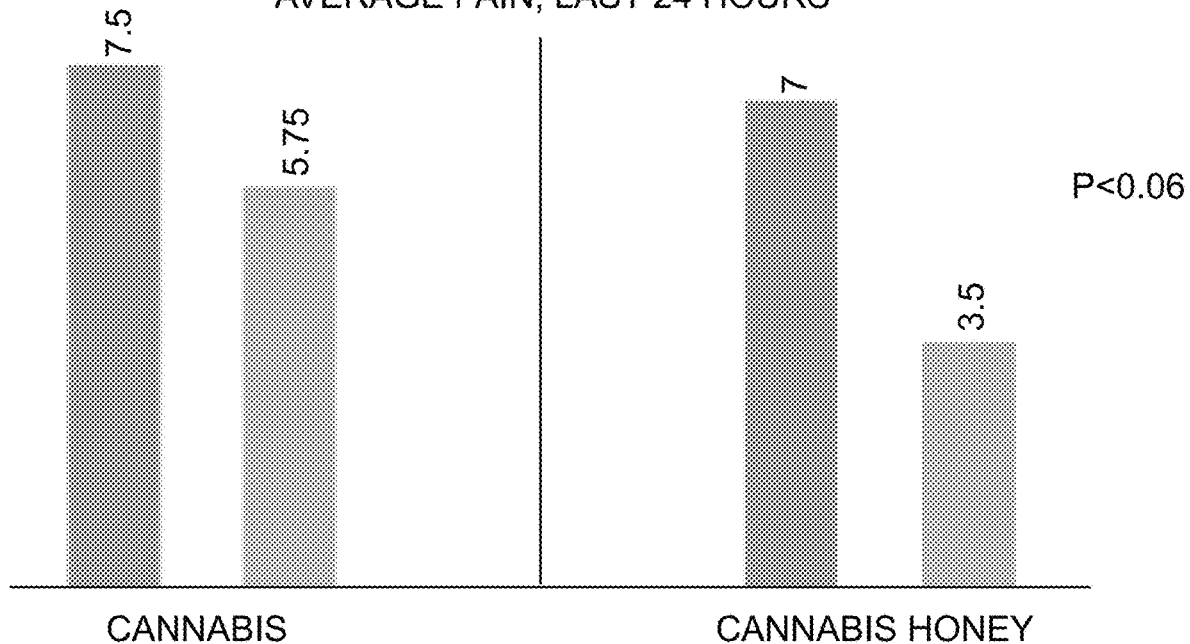
FIG. 3 is a graph showing changes in average pain during 24 hours in fibromyalgia patients—t-test showing statistical trend in *cannabis* honey group. Orange bars: average of questioner #I and average of questioner #III. Grey bars: average of questioner #II and average of questioner #IV.
Figure 4:
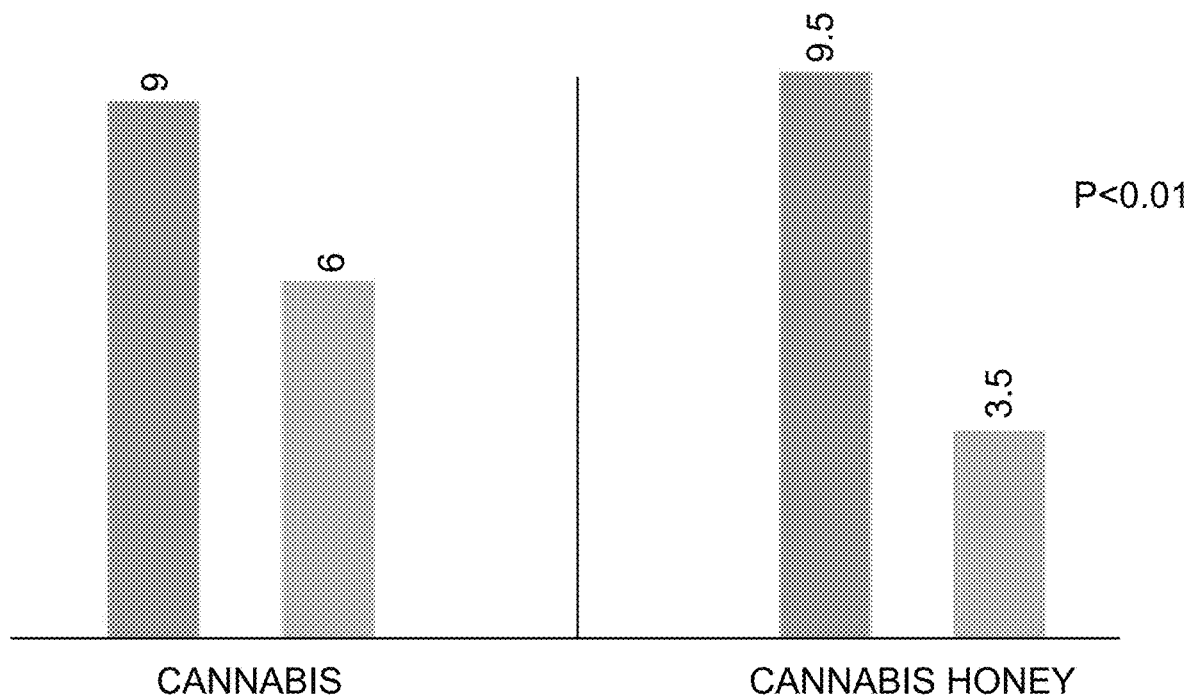
FIG. 4 is a graph showing changes in knee local pain during 24 hours in fibromyalgia patients—t-test showing statistically significant improvement in *cannabis* honey group. Orange bars: average of questioner #I and average of questioner #III. Grey bars: average of questioner #II and average of questioner #IV.
Figure 5:
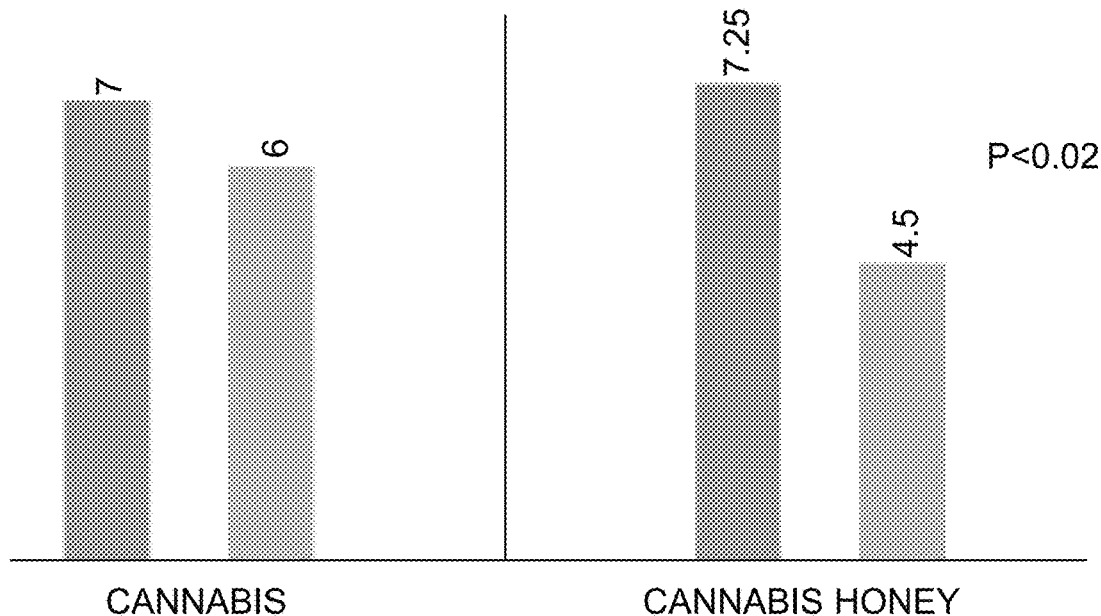
FIG. 5 is a graph showing changes in general activity limitation during 24 hours in fibromyalgia patients—t-test showing statistically significant improvement in *cannabis* honey group. Orange bars: average of questioner #I and average of questioner #III. Grey bars: average of questioner #II and average of questioner #IV.
Figure 6:
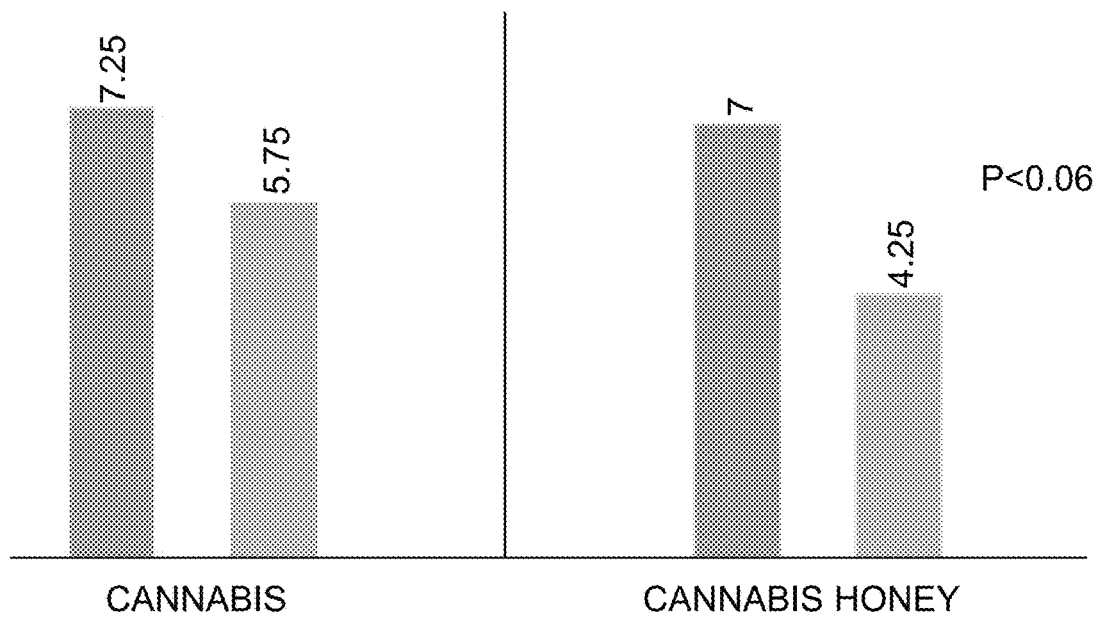
FIG. 6 is a graph showing changes in walking limitation during 24 hours in fibromyalgia patients—t-test showing statistical trend in *cannabis* honey group. Orange bars: average of questioner #I and average of questioner #III. Grey bars: average of questioner #II and average of questioner #IV.
Figure 7:
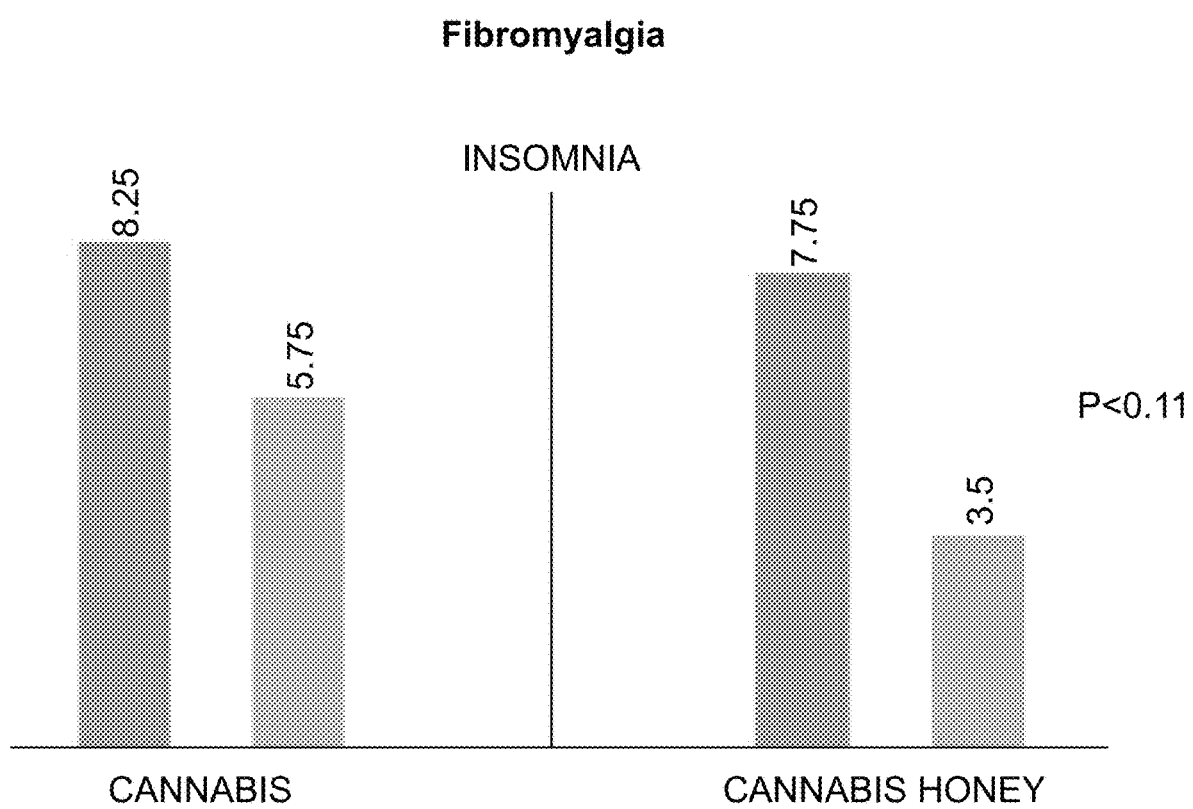
FIG. 7 is a graph showing changes in insomnia during 24 hours in fibromyalgia patients—t-test showing statistical trend in *cannabis* honey group. Orange bars: average of questioner #I and average of questioner #III. Grey bars: average of questioner #II and average of questioner #IV.
Figure 8:
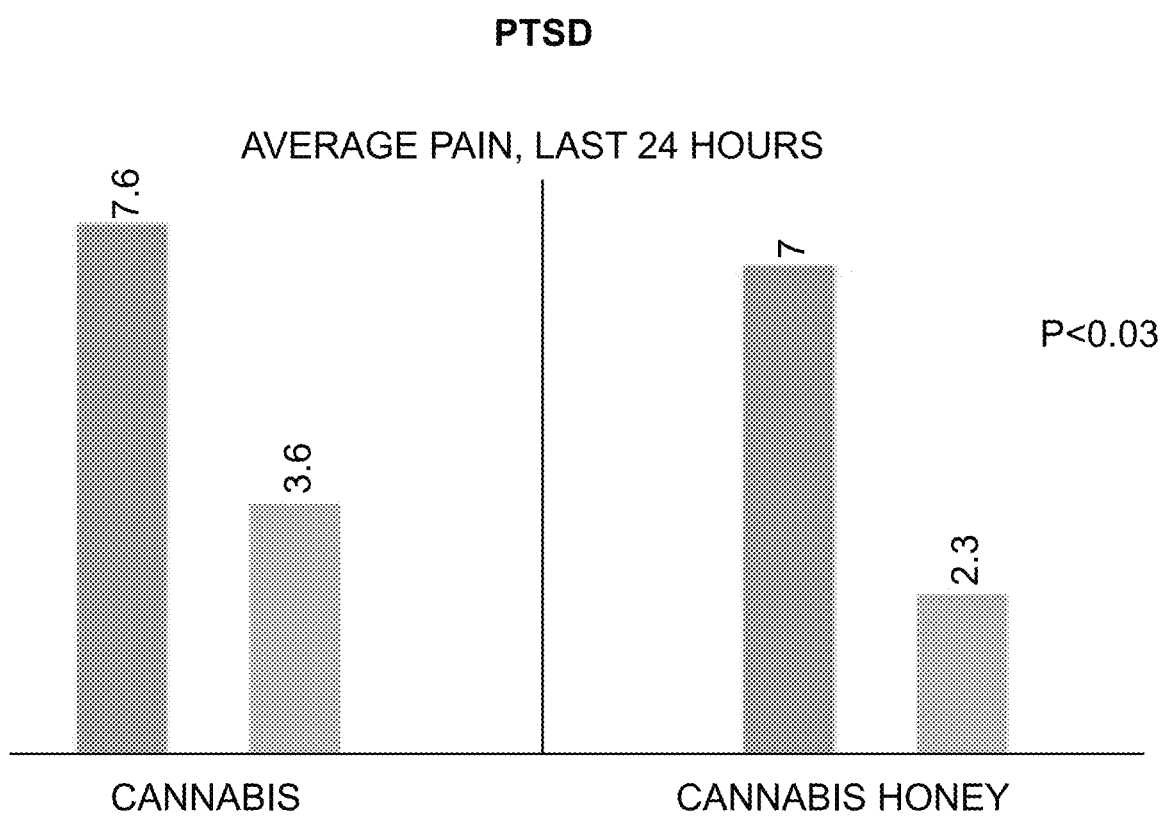
FIG. 8 is a graph showing changes in average pain during 24 hours in PTSD patients—t-test showing statistical significant change in *cannabis* honey group.
Figure 9:
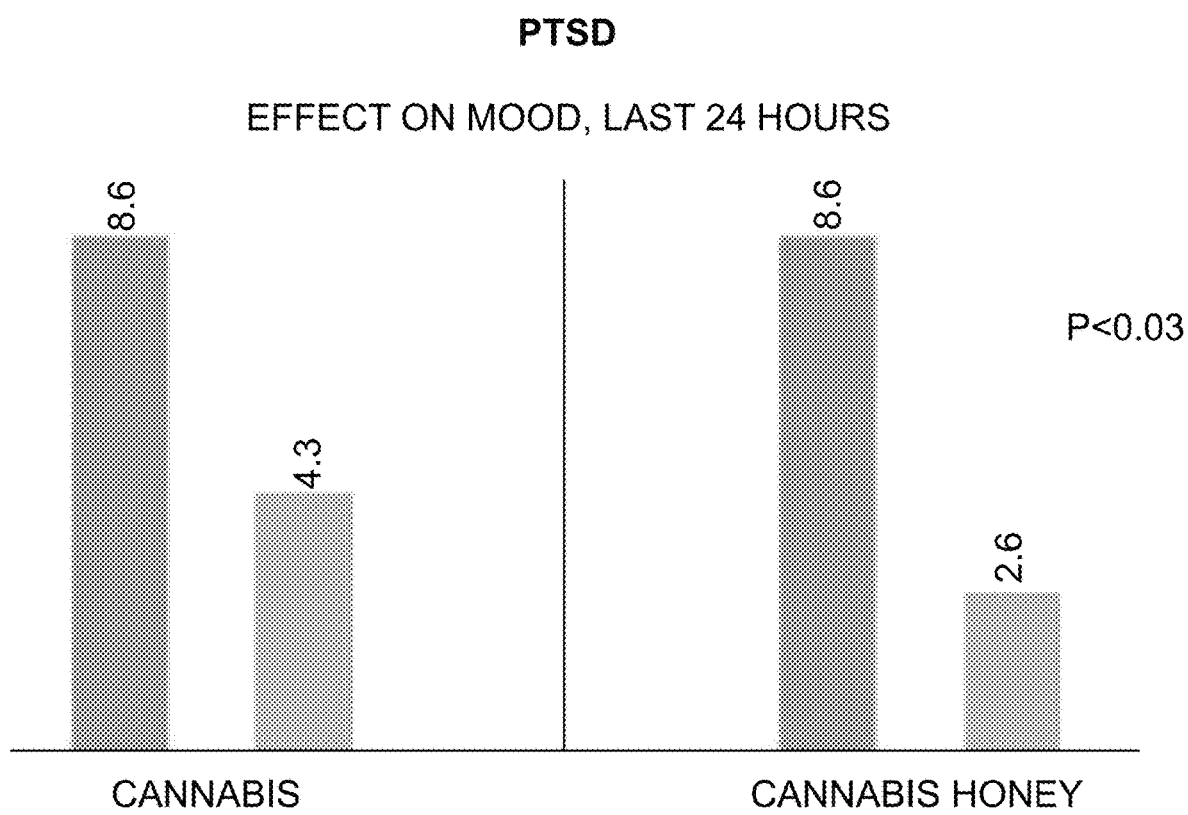
FIG. 9 is a graph showing changes in effect on mood during 24 hours in PTSD patients—t-test showing statistical significant change in *cannabis* honey group. Orange bars: average of questioner #I and average of questioner #III. Grey bars: average of questioner #II and average of questioner #IV.
Figure 10:
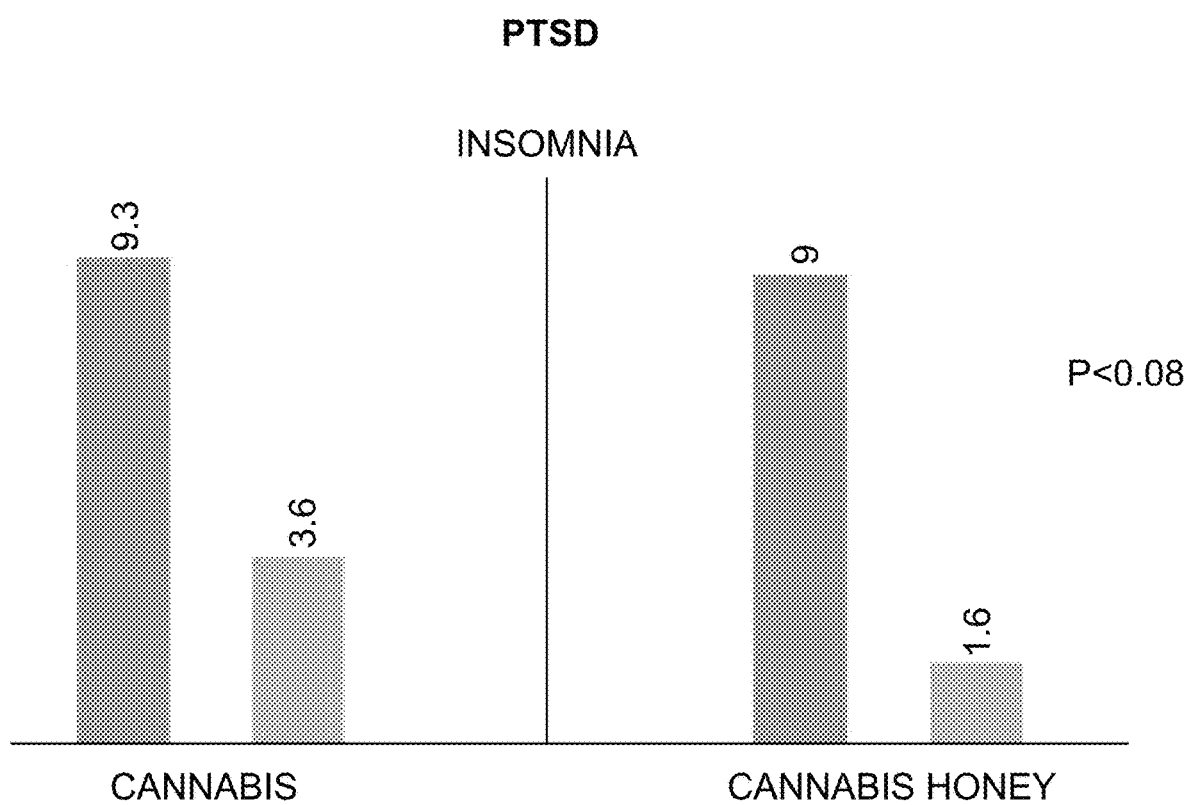
FIG. 10 is a graph showing changes in effect on mood during 24 hours in PTSD patients—t-test showing statistical significant change in *cannabis* honey group. Orange bars: average of questioner #I and average of questioner #III. Grey bars: average of questioner #II and average of questioner #IV.

The present invention, in some embodiments thereof, relates to bee-ingestible compositions, methods of using same for producing honey and honey produced thereby.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

*Cannabis*, also known as marijuana and by numerous other names, is a preparation of the *Cannabis* plant intended for use as a psychoactive drug or medicine. The main psychoactive part of *cannabis* is tetrahydrocannabinol (THC); it is one of 483 known compounds in the plant, including at least 84 other cannabinoids, such as cannabidiol (CBD), cannabinol (CBN), tetrahydrocannabivarin (THCV).

*Cannabis* has been indicated for the reduction of nausea and vomiting during chemotherapy, improving appetite in people with HIV/AIDS, alleviation of chronic pain and muscle spasms as well as other medical conditions such as detailed hereinbelow.

Since the beginning of the twentieth century, most countries have enacted laws against the cultivation, possession or transfer of *cannabis*. There presently exists a need to provide more effective and safer *cannabis* preparations for various medical uses.

While reducing the present invention to practice, the present inventor was able to feed honeybees on *cannabis* oil extract. This finding is particularly surprising since it is well known in the beekeeping world that honeybees do not pollinate *cannabis*. In fact, *cannabis* is naturally pollinated by wind, hence the plant does not produce nectar which is so essential to bees as a carbohydrate and protein source.

However, according to the present teachings, bee ingestible compositions comprising the *cannabis* oil are fed to the bees which in turn produce honey which comprises the active ingredients in the *cannabis* oil e.g., cannabinoids. Despite the lower concentration of the active ingredients in the honey thus produced, the honey is endowed with pharmaceutical activity absent from control honey, i.e., honey simply mixed with the active ingredients at the corresponding concentration. Thus, the present findings pave the way to the production of honey and honey-based products which are effective and safe for various medical uses.

Thus, according to an aspect of the invention there is provided a bee ingestible composition comprising a bee food base and CBD and/or THC.

As used herein the term "bee" refers to any of several winged, hairy-bodied, usually stinging insects of the superfamily Apoidea in the order Hymenoptera, including both solitary and social species and characterized by sucking and chewing mouthparts for gathering nectar, as well as collecting pollen. Exemplary bee species include, but are not limited to *Apis, Bombus, Trigona, Osmia* and the like. In one embodiment, bees include, but are not limited to bumblebees (*Bombus terrestris*) and honeybees (*Apis mellifera*). It is believed that the present teachings are relevant to the aforementioned bee species. However, due to the commercial interest more emphasis has been put on honey bees. The term as used herein refers to a bee at any developmental stage, e.g., egg larvae and pupa, adult e.g., queen, workers and drones. According to a specific embodiment, the bee is an adult bee.

According to a specific embodiment, the term "honeybee" or "honey bee" refers to the western honey bee or European honey bee (*Apis mellifera*), being a species of bee.

As used herein the term "bee ingestible composition" also referred to herein as "the composition" refers to a natural or non-natural bee feed which is transferred to the nectar sac (for honey production) and optionally to the stomach.

According to a specific embodiment, the composition is in a solid form e.g., pollen cake.

According to a specific embodiment, the composition is in a semi-solid form.

According to a specific embodiment, the composition is in liquid form.

According to a specific embodiment, the liquid is a sucrose solution.

According to a specific embodiment, the liquid is a corn syrup solution.

According to a specific embodiment, the composition is a paste.

According to a specific embodiment, the liquid further comprises a carbohydrate or sugar supplement.

According to a specific embodiment, a bee food base of the bee ingestible composition comprises a natural bee feed.

According to a specific embodiment, a bee food base of the bee ingestible composition comprises a non-natural bee feed.

According to a specific embodiment, the bee food base is selected from the group consisting of honey, pollen, nectar, a carbohydrate solution and mixtures thereof.

According to a specific embodiment, the bee food base is selected from the group consisting of wheat, soybean flour, yeast, corn syrup, beet sugar syrup, isomerized corn syrup and type-50 sugar syrup.

According to a specific embodiment, the bee food base in the composition is honey.

According to a specific embodiment, the bee ingestible composition as described herein comprises oil for rendering the composition more fluid.

According to a specific embodiment, the oil is derived from wheat germ, Camelina, Jojova, macroloba, *Passiflora edulis, Mauritia flexuosa*, Carpa, Brazil nut, *Astrocaryum aculeum, Annona muricata, Acmella oleracea*, Acai palm, Sesame, Rice bran, Linseed, Hazelnut, Grape seed, Corn, Coconut, Palm kernel, Cottonseed, Peanut, Canola, Sunflower seed High Oleic, Sunflower seed High Linoleic, Rapeseed, Soybean and Palm.

According to a specific embodiment, the oil is olive oil.

As used herein the term "cannabidiol" or "CBD" refers to the major non-psychotropic cannabinoid in most *Cannabis* preparations, such as hashish and marihuana. Thus, cannabidiol, as used herein, is meant to refer to 2-[3-methyl-6-

(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors of 2-[3-methyl-6-(1-methylethenyl)-2-cyclohexen-1-yl]-5-pentyl-1,3-benzenediol. The synthesis of 2-[3-methyl-6-(1-methylethenyl)-2-cyclohexen-1-yl]-5-pentyl-1,3-benzenediol is described, for example, in Petilka et al., Helv. Chim. Acta, 52:1102 (1969) and in Mechoulam et al., J. Am. Chem. Soc., 87:3273 (1965), which are hereby incorporated by reference.

The term CBD refers to the naturally occurring substance or synthetic versions of same. The term also refers to cannabidiol derivatives and metabolites such as taught in U.S. Pat. Nos. 7,759,526, 8,119,697 and 8,435,556 each of which is hereby incorporated by reference in its entirety.

As used herein the term "THC" or Tetrahydrocannabinol, or more precisely its main isomer (−)-trans-$\Delta^9$-tetrahydrocannabinol ((6aR,10aR)-delta-9-tetrahydrocannabinol), is the principal psychoactive constituent (or cannabinoid) of *cannabis*. The term refers to the naturally occurring substance or synthetic versions of same.

"(−)-trans-$\Delta^9$-tetrahydrocannabinol", as used herein, also refers to its pharmaceutically acceptable salts, solvates, metabolites, and metabolic precursors. .DELTA..sup.9-tetrahydrocannabinol is marketed under the generic name "dronabinol".

As mentioned the THC and/or CBD can be provided into the composition in a purified form (e.g., above 90% purity each, e.g., synthetic forms) or in a *cannabis* oil (e.g., trichome extract). The *cannabis* oil should not be confused with the oil described above.

The oil can be extracted from a single genetic background of a *cannabis* plant i.e., line, or a plurality of genetic backgrounds.

As used herein the term "*cannabis*" refers to the genus of flowering plants that includes three different species, *Cannabis sativa, Cannabis* indica and *Cannabis ruderalis*.

According to a specific embodiment, the *cannabis* is from the species *Cannabis ruderalis* which is substantially devoid of psychotrophic activity.

When *cannabis* oil is used, as the source of CBD/THC, the composition comprises also other metabolites and active ingredients which are extracted in the *cannabis* oil. Examples include but are not limited to other cannabinoids as well as terpenes, flavinoids etc. Such compounds are easily identified using gas chromatography or HPLC (see for details Romano et al. Cannabinoids 2013; 1(1):1-11).

When *cannabis* oil is used, the *cannabis* genetic background is selected according to the intended use, that is, high/low CBD/THC levels.

For example, breeders are currently developing more CBD-rich strains, as reported in Good, Alastair (26 Oct. 2010). "Growing marijuana that won't get you high". *The Daily Telegraph* (London). Other CBD-reach strains are available from Tikun Olam that developed a strain of the plant which has only cannabidiol as an active ingredient, and no detectable levels of THC, providing some of the medicinal benefits of *cannabis* without the psychotrophic effects. Avidekel, a *cannabis* strain that contains 15.8% CBD and less than 1% THC can also be used according to the present teachings. Alternatively, strains of *cannabis* containing higher levels of THC than levels of (or no) CBD may be desirable for treating certain medical conditions, such as, for example, conditions causing chronic pain.

According to a specific embodiment, any variety of *cannabis* and/or hemp may be used provided that is a minimum of 1% CBD and/or THC.

Numerous methods are known in the art to extract oil from the *cannabis* plant and the ordinary skilled artisan will know which to choose according to the intended use. Examples of CBD/THC extraction methods include, but are not limited to, $CO_2$ extraction, alcohol (e.g., ethanol) extraction, and oil extraction (e.g., olive oil extraction). In the latter, various oils can be used, including. but not limited to, vegetable oils, nut oils, butter and the like. Specific examples include, but are not limited to, almond, avocado, butter, canola, coconut oil, grape seed oil, hemp seed oil, olive, pecan, sesame, and walnut oils.

Thus even if the oil is extracted using methods which do not involve oil extraction, oil may be added to the composition to render it more fluid and to dilute the active ingredients such as by a factor of 10-200 (e.g., 100 fold), dependent on the composition of cannabinoids in the *cannabis* oil and the intended use.

According to an alternative or an additional embodiment, lecithin is added to the composition as an emulsifier when the sugar base is not sourced from honey.

Since the present teachings relate to the production of bee products which are endowed with pharmaceutical activities, the composition may further comprise other pharmaceuticals. Such pharmaceuticals can be phytochemicals provided in the composition either in a purified form (e.g., synthetic) or as part of an herbal extract.

According to a specific embodiment the pharmaceutical is selected from the group consisting of an anti-allergic agent, an anti-inflammatory agent, an antioxidant, an anti-microbial agent, an antibacterial agent, an antifungal agent, an antiviral agent, an analgesic agent, an anti-cancer agent, an apoptosis inducing agent and an anti-diarrheal agent.

According to a specific embodiment, the pharmaceutical is not an analgesic agent.

According to a specific embodiment, the extracts are polar or non-polar and/or hydrophobic or hydrophilic extracts. Non-limiting examples of suitable plant extracts are those from *Echinacea, Uncaria, Eleuther ococcus, Urtica, Calendula*, Trifoluim, Melissa, Moms, *Ribes, Taraxacum, Chicorium, Vaccinium, Avena*, Inula, Melilotus, *Ficus*, and Beta.

Examples of such phytochemicals include, but are not limited to, terpenoids, flavonoids, tannins, phenols, saponins, polyphenols, heterosides and alkaloids.

Examples of medicinal plants from which active ingredients may be extracted include, but are not limited to, *Salvia sclarea, Echinacea purpurea*, extracts from citruses. Examples of active ingredients include, but are not limited to, Heterosides: Anthraquinones, cardiac glycosides, cyanogenics; Coumarins Flavonids phenols, ranunculosides, saponosides, sulphurides; Polyphenoles: Phenolic acids, cumarins, flavonoids, lignans, tannins, quinine; and Terpenoids: Essential oils, iridoids, lactones, diterpones, saponins. Alkaloids.

According to a specific embodiment, the flavanoid is naringin. Naringin is a flavanone-7-O-glycoside between the flavanone Naringenin and the disaccharide neohesperidose. The flavonoids naringenin and hesperetin, which form the aglycones of naringin and hesperidin, occur naturally in citrus fruits, especially in grapefruit, where naringin is responsible for the fruit's bitter taste. Naringin is indicated as an inhibitor of vascular endothelial growth factor (VEGF) release. Naringin reduces diabetes-induced neuropathy. Naringin ameliorates memory deficits in Alzheimer's disease through attenuating mitochondrial dysfunction. Naringin has shown protective effects against cognitive dysfunction and oxidative damage.

According to a specific embodiment, the pharmaceutical may be a plant-derived pharmaceutical, also referred to herein as a phytochemical.

According to a specific embodiment, the pharmaceutical is not naturally present in (i.e., endogenous to) the *cannabis* trichome or *cannabis* oil.

It will be appreciated that other ingredients may be added to the bee ingestible composition. Such ingredients may include, but are not limited to, coloring agents, emulsifiers, plant extracts with medical uses, flavors, and protein.

The doses of the CBD and/or THC in the bee-ingestible composition may vary according to the intended use.

For example, CBD finds use in neurological applications (e.g., neurodegenerative disorders such as Alzheimer's disease and Parkinson) as well as inflammation due to its neuroprotective activity and anti-oxidative activity. CBD has anti-psychotic effects and counteracts the potential psychotomimetic effects of THC on individuals with latent schizophrenia and other mood disorders such as bipolar mood disorder, anxiety and more. The compound has been shown to be an alternative treatment for schizophrenia that is safe and well-tolerated. Cannabidiol has also been shown to reduce anxiety in social anxiety disorder. Chronic cannabidiol administration in rats was found to produce anxiogenic-like effects, indicating that prolonged treatment with cannabidiol incite anxiogenic effects. Cannabidiol also finds use is the treatment of epilepsy e.g., Dravet syndrome. CBD is also indicated for use in the treatment of inflammation and can be used for treating diseases such as rheumatoid arthritis, colitis, liver inflammation, heart disease and diabetes.

THC finds use in Multiple sclerosis symptoms:

Spasticity, based on the results of high quality trials, oral *cannabis* extract was rated as effective, and THC as probably effective, for improving patient's subjective experience of spasticity. Oral *cannabis* extract and THC both were rated as possibly effective for improving objective measures of spasticity (Koppel B S, Brust J C, Fife T, Bronstein J, Youssof S, Gronseth G, Gloss D (April 2014). "Systematic review: Efficacy and safety of medical marijuana in selected neurologic disorders: Report of the Guideline Development Subcommittee of the American Academy of Neurology". Neurology 82 (17): 1556-63).

Centrally mediated pain and painful spasms. Based on the results of high quality trials, oral *cannabis* extract was rated as effective, and THC as probably effective in treating central pain and painful spasms (Koppel, supra).

Neurodegenerative disorders in which *cannabis* and THC were recently indicated include, Huntington disease, Parkinson disease. (e.g., ameliorating levodopa-induced dyskinesia in Parkinson disease), Alzheimer's disease, and other neurological disorders including but not limited to Tourette syndrome, Cervical dystonia and epilepsy.

THC helps alleviating symptoms suffered both by AIDS patients, and by cancer patients undergoing chemotherapy, by increasing appetite and decreasing nausea. It has also been shown to assist some glaucoma patients by reducing pressure within the eye, and is used in alleviating neuropathic pain and spasticity.

Exemplary embodiments of the composition of the present invention are listed below.

According to a specific embodiment, the composition comprises 50-99.9% bee food base (e.g., honey).

According to a specific embodiment, the composition comprises 60-99.9% bee food base (e.g., honey).

According to a specific embodiment, the composition comprises 70-99.9% bee food base (e.g., honey).

According to a specific embodiment, the composition comprises 80-99.9% bee food base (e.g., honey).

According to a specific embodiment, the composition comprises 90-99.9% bee food base (e.g., honey).

According to a specific embodiment, the composition comprises 50-90% bee food base (e.g., honey).

According to a specific embodiment, the composition comprises 60-80% bee food base (e.g., honey).

According to a specific embodiment, the composition comprises 65-70% bee food base (e.g., honey).

According to a specific embodiment, the composition comprises 60-70% bee food base (e.g., honey).

According to a specific embodiment, the composition comprises 60-95% bee food base (e.g., honey).

According to a specific embodiment, the composition comprises 70-95% bee food base (e.g., honey).

According to a specific embodiment, the composition comprises 80-95% bee food base (e.g., honey).

According to a specific embodiment, the composition comprises 90-95% bee food base (e.g., honey).

According to a specific embodiment, the composition comprises 95-99.9% bee food base (e.g., honey).

According to a specific embodiment, the composition comprises 96-99.9% bee food base (e.g., honey).

According to a specific embodiment, the composition comprises 97-99.9% bee food base (e.g., honey).

According to a specific embodiment, the composition comprises 95-99% bee food base (e.g., honey).

According to a specific embodiment, the composition comprises 97-99% bee food base (e.g., honey).

According to a specific embodiment, the composition comprises 98-99% bee food base (e.g., honey).

According to a specific embodiment, the composition comprises 50-99.9% honey.

According to a specific embodiment, the composition comprises 60-99.9% honey.

According to a specific embodiment, the composition comprises 65-99.9% honey.

According to a specific embodiment, the composition comprises 70-99.9% honey.

According to a specific embodiment, the composition comprises 80-99.9% honey.

According to a specific embodiment, the composition comprises 90-99.9% honey.

According to a specific embodiment, the composition comprises 50-90% honey.

According to a specific embodiment, the composition comprises 60-80% honey.

According to a specific embodiment, the composition comprises 65-70% honey.

According to a specific embodiment, the composition comprises 60-70% honey.

According to a specific embodiment, the composition comprises 60-95% honey.

According to a specific embodiment, the composition comprises 70-95% honey.

According to a specific embodiment, the composition comprises 80-95% honey.

According to a specific embodiment, the composition comprises 90-95% honey.

According to a specific embodiment, the composition comprises 95-99.9% honey.

According to a specific embodiment, the composition comprises 96-99.9% honey.

According to a specific embodiment, the composition comprises 97-99.9% honey.

According to a specific embodiment, the composition comprises 95-99% honey.

According to a specific embodiment, the composition comprises 97-99% honey.

According to a specific embodiment, the composition comprises 98-99% honey.

According to a specific embodiment, the composition comprises 0.1-5% *cannabis* oil.

According to a specific embodiment, the composition comprises 0.1-4% *cannabis* oil.

According to a specific embodiment, the composition comprises 0.1-3% *cannabis* oil.

According to a specific embodiment, the composition comprises 0.1-2% *cannabis* oil.

According to a specific embodiment, the composition comprises 0.1-1% *cannabis* oil.

According to a specific embodiment, the composition comprises 0.1-0.9% *cannabis* oil.

According to a specific embodiment, the composition comprises 0.1-0.8% *cannabis* oil.

According to a specific embodiment, the composition comprises 0.1-0.7% *cannabis* oil.

According to a specific embodiment, the composition comprises 0.1-0.6% *cannabis* oil.

According to a specific embodiment, the composition comprises 0.1-0.5% *cannabis* oil.

According to a specific embodiment, the composition comprises 0.1-0.3% *cannabis* oil.

According to a specific embodiment, the composition comprises 0.1-0.2% *cannabis* oil.

According to a specific embodiment, the composition comprises 10-600 mg/g THC and/or CBD.

According to a specific embodiment, the composition comprises 10-200 mg/gr THC and/or CBD.

According to a specific embodiment, the composition comprises 10-100 mg/gr THC and/or CBD.

According to a specific embodiment, the composition comprises 50-100 mg/gr THC and/or CBD.

Optionally, as mentioned, the composition comprises at least one pharmaceutical (e.g., which is not naturally present in the *cannabis* oil).

According to a specific embodiment, the composition comprises 0.1-1% pharmaceutical.

According to a specific embodiment, the composition comprises 0.1-0.9% pharmaceutical.

According to a specific embodiment, the composition comprises 0.1-0.8% pharmaceutical.

According to a specific embodiment, the composition comprises 0.1-0.7% pharmaceutical.

According to a specific embodiment, the composition comprises 0.1-0.6% pharmaceutical.

According to a specific embodiment, the composition comprises 0.1-0.5% pharmaceutical.

According to a specific embodiment, the composition comprises 0.1-0.3% pharmaceutical.

According to a specific embodiment, the composition comprises 0.1-0.2% pharmaceutical.

According to a specific embodiment, the bee food base is present in the composition at an amount of at least 50%.

According to a specific embodiment, the bee food base is present in the composition at an amount of at least 60%.

According to a specific embodiment, the bee food base is present in the composition at an amount of at least 65%.

According to a specific embodiment, the bee food base is present in the composition at an amount of at least 70%.

According to a specific embodiment, the bee food base is present in the composition at an amount of at least 80%.

According to a specific embodiment, the bee food base is present in the composition at an amount of at least 90%.

According to a specific embodiment, the bee food base is present in the composition at an amount of at least 95%.

According to a specific embodiment, the bee food base is present in the composition at an amount of at least 96%.

According to a specific embodiment, the bee food base is present in the composition at an amount of at least 97%.

According to a specific embodiment, the bee food base is present in the composition at an amount of at least 98%.

According to a specific embodiment, the bee food base is present in the composition at an amount of at least 99%.

According to a specific embodiment, the bee food base is present in the composition at an amount of at least 99.1%.

According to a specific embodiment, the bee food base is present in the composition at an amount of at least 99.2%.

According to a specific embodiment, the bee food base is present in the composition at an amount of at least 99.3%.

According to a specific embodiment, the bee food base is present in the composition at an amount of at least 99.4%.

According to a specific embodiment, the bee food base is present in the composition at an amount of at least 99.5%.

According to a specific embodiment, the bee food base is present in the composition at an amount of at least 99.6%.

According to a specific embodiment, the bee food base is present in the composition at an amount of at least 99.7%.

According to a specific embodiment, the bee food base is present in the composition at an amount of at least 99.8%.

According to a specific embodiment, the *cannabis* oil is present in the bee-ingestible composition at an amount not exceeding 1%.

According to a specific embodiment, the *cannabis* oil is present in the bee-ingestible composition at an amount not exceeding 0.9%.

According to a specific embodiment, the *cannabis* oil is present in the bee-ingestible composition at an amount not exceeding 0.8%.

According to a specific embodiment, the *cannabis* oil is present in the bee-ingestible composition at an amount not exceeding 0.7%.

According to a specific embodiment, the *cannabis* oil is present in the bee-ingestible composition at an amount not exceeding 0.6%.

According to a specific embodiment, the *cannabis* oil is present in the bee-ingestible composition at an amount not exceeding 0.5%.

According to a specific embodiment, the *cannabis* oil is present in the bee-ingestible composition at an amount not exceeding 0.4%.

According to a specific embodiment, the *cannabis* oil is present in the bee-ingestible composition at an amount not exceeding 0.3%.

According to a specific embodiment, the *cannabis* oil is present in the bee-ingestible composition at an amount not exceeding 0.2%.

Of note, water can be added to the composition in order to dilute the active ingredients.

According to a specific embodiment, the water portion does not exceed 50%.

According to a specific embodiment, the water portion does not exceed 45%.

According to a specific embodiment, the water portion does not exceed 40%.

According to a specific embodiment, the water portion does not exceed 35%.

According to a specific embodiment, the water portion does not exceed 25%.

According to a specific embodiment, the water portion does not exceed 15%.

According to a specific embodiment, the composition comprises:

50-99.9% bee food base;
0.1-1% *cannabis* oil; and optionally
0.1-1% pharmaceutical.

The composition is typically prepared by mixing the THC/CBD (e.g., *cannabis* oil), optionally diluted in oil (e.g., olive oil) or emulsifier, with the pharmaceutical (when present). In a separate mix, honey and water are combined till 100%, Other ingredients such as described hereinabove can be added.

Of note all percentages indicated herein refer to w/w, v/v, v/w or w/v.

A non-limiting protocol is provided infra and in Example 1 that follows. A liquid mixture containing honey [or glucose, beet sugar, honey substitutes, or treacle (molasses)] and water (e.g., two parts honey and one part water) is prepared. The composition is mixed by shaking.

Once the honey and water mixture is prepared, *cannabis* oil and/or *cannabis* hemp flowers in the form of a cake or powder are added. Finally, other ingredients such as natural coloring agents are added.

The components are mixed until reaching a homogeneous composition. According to a specific embodiment, mixing is done while heating (e.g., to 75° C.).

After preparation, the mixture is allowed to cool to room temperature, and poured it into a bee feeding station according to the capacity of the feeding station. The feeding cycle depends on the capacity of the feeding station and the size of the bee hive.

The bee ingestible composition can be delivered to the bees in a great variety of ways. As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheat (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. The last two can be supplied only as a liquid to bees.

Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one embodiment, pan or trays in which floating supports—such as wood chips, cork, or plastic sponge—are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413).

As the honey comprises the active ingredients fed to the bees, there is also provided herein a method of producing honey. The method comprises:

(a) feeding the bees with the bee ingestible composition as describe herein; and or concomitantly
(b) collecting the honey produced by the bees.

Honey extraction is done after or concomitantly with feeding with the bee ingestible composition using methods which are well known to those skilled in the tradition of beekeeping. Measures are taken to feed the bees with the composition at the time of honey production, while restricting their accessibility to field nectar/pollen.

Those of skills in the art of beekeeping will know to time the extraction.

According to some embodiments of the invention, and as orally administered compositions are also evident in the honey (albeit in far lower concentrations than initially administered 1000 fold reduction), the present teachings also contemplate a processed product comprising the honey obtainable according to the present teachings.

Thus, according to an aspect of the invention there is provided honey obtainable according to the methods described herein.

The honey may comprise any *cannabis* oil metabolite, e.g., cannabinoid, e.g., THC and/or CBD.

According to a specific embodiment, the honey is free of plant material e.g., cellulose.

According to a further aspect there is provided honey comprising THC and/or CBD and optionally a pharmaceutical which is not-naturally present in *cannabis* as described herein.

According to some embodiments of the invention, the honey is characterized in that it comprises about 1,000 or more fold lower (e.g., about 10,000 fold lower) concentration of THC and/or CBD than that present in the *cannabis* oil used to prepare said bee-ingestible composition, and about 4 or more fold lower concentration of THC and/or CBD than the bee-ingestible composition itself. Measurements can be made using methods which are well known in the art such as liquid chromatography.

According to a specific embodiment, the honey is characterized in that it comprises 4-10 fold lower concentration of THC and/or CBD (and/or the pharmaceutical) than that present in the bee-ingestible composition.

According to a specific embodiment, the honey is characterized in that it comprises 4-8 fold lower concentration of THC and/or CBD (and/or the pharmaceutical) than that present in the bee-ingestible composition.

According to a specific embodiment, the honey is characterized in that it comprises 4-6 fold lower concentration of THC and/or CBD (and/or the pharmaceutical) than that present in the bee-ingestible composition.

According to a specific embodiment, the honey is characterized in that it comprises 3-6 fold lower concentration of THC and/or CBD (and/or the pharmaceutical) than that present in the bee-ingestible composition.

According to an aspect of some embodiments of the present invention there is provided honey comprising 5 ppm-500 ppm THC and/or CBD.

According to an aspect of some embodiments of the present invention there is provided honey comprising 5 ppm-400 ppm THC and/or CBD.

According to an aspect of some embodiments of the present invention there is provided honey comprising 5 ppm-300 ppm THC and/or CBD.

According to a further aspect, there is provided honey which is characterized in that it comprises 10 ppm-200 ppm THC and/or CBD.

According to a specific embodiment, the honey is characterized in that it comprises 50 ppm-100 ppm THC and/or CBD.

According to a specific embodiment, the honey is characterized in that it comprises 50 ppm-80 ppm THC and/or CBD.

According to a specific embodiment, the honey is characterized in that it comprises a pharmaceutical.

According to one embodiment the honey is in a semi-solid form.

According to one embodiment the honey is in a solid form.

According to one embodiment the honey is in a liquid form.

Throughout this specification, the term honey is used to include any honey-like beehive product, including those that do not fulfill the nutritional definitions of honey as defined by some food regulatory authorities. Natural honey as defined by the National Honey Board of the United States (www(dot)nhb(dot)org) will be referred to as "pure honey" or "regular honey".

However, the honey serving as the bee food base is pure honey.

A processed product comprising the honeybee products are also contemplated herein e.g., cakes, cookies, bars, candy, grains, chewable honey (e.g., U.S. Pat. No. 8,642,103).

According to a further aspect of the invention, there is provided a method of treating a medical condition which is alleviated by *cannabis*, the method comprising administering to a subject in need thereof a therapeutically effective amount of the honey or a processed product thereof as described herein, thereby treating the medical condition which is alleviated by *cannabis*.

According to a specific embodiment, the medical condition is selected from the group consisting of nausea and pain associated with cancer and chemotherapy; nausea, pain and wasting associated with AIDS; arthritis and rheumatism; glaucoma; migraine; muscle spasticity associated with multiple sclerosis and paralysis; alcohol and narcotics withdrawal; stress; depression; asthma; epileptic seizures, dementia, diabetes, neuropathic pain or diseases associated therewith, and other medical conditions described throughout the specification.

Additional examples include, but are not limited to fibromyalgia and posttraumatic stress disorder (PTSD) and pain associated therewith.

According to a specific embodiment, the subject treated with the composition is a human being, though veterinary indications are also contemplated herein.

The subject may suffer from the disease or be at risk of having it. The subject may be of any gender or age. According to a specific embodiment, the subject is 75 years of age or older.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Feeding Protocols

A feeding protocol was developed aiming to find the range of concentrations of *Cannabis* oils, Naringin, honey and water suitable for honey bee consumption (A).

A similar feeding protocol aimed at finding the range of concentrations of honey, water, natural coloring agents, and *cannabis* oil optimal for honey bee consumption (B).

Generally, honey was mixed by shaking with water at the indicated positions. Once the honey and water mixture was prepared, *cannabis* oil was added. A pre-produced *cannabis* oil was used from IMC Agro Ltd. Finally, several other components were added to the mixture, such as lecithin (an emulsifier), and various coloring agents, such as beet juice and beet extract, paprika, and tomato peel extract, and royal jelly, which is a bee feed component.

The components were mixed until a homogeneous mixture was produced. While mixing, the mixture was heated to 75° C.

After preparation, the mixture was allowed to cool to room temperature, and poured it into a bee feeding station according to the capacity of the feeding station. The feeding cycle depends on the capacity of the feeding station and the size of the bee hive.

The treatments were offered to the honey bees in small cans or feeding troughs and attraction data was collected (see FIG. 1 and Table 1A for protocol A, Table 1B for Protocol B, below).

Protocol A:

The following parameters were applied:
1. Naringin 98% purity diluted in water.
2. *Cannabis* oil % in the protocol.
3. Different ratios of CBD and THC in the full profile of *Cannabis* extracts.
4. % of honey in the protocol as part of the total honey and water quantity.
5. % of water in the protocol as part of the total honey and water quantity.

TABLE 1A

| # | Naringin % w/w | Cannabis oil % w/w | CBD/THC ratio w/w | Honey % w/w | water % w/w | attraction 1-10 |
|---|---|---|---|---|---|---|
| 1 | 2 | 1 | 5/1 | 55 | 45 | 1 |
| 2 | 2 | 0.5 | 2/1 | 60 | 40 | 1 |
| 3 | 2 | 0.25 | 1/1 | 65 | 35 | 3 |
| 4 | 2 | 0.2 | 1/2 | 70 | 30 | 4 |
| 5 | 2 | 0.1 | 1/3 | 75 | 25 | 4 |
| 6 | 1 | 1 | 5/1 | 55 | 45 | 3 |
| 7 | 1 | 0.5 | 2/1 | 60 | 40 | 3 |
| 8 | 1 | 0.25 | 1/1 | 65 | 35 | 5 |
| 9 | 1 | 0.2 | 1/2 | 70 | 30 | 6 |
| 10 | 1 | 0.1 | 1/3 | 75 | 25 | 6 |
| 11 | 0.5 | 1 | 5/1 | 55 | 45 | 4 |
| 12 | 0.5 | 0.5 | 2/1 | 60 | 40 | 4 |
| 13 | 0.5 | 0.25 | 1/1 | 65 | 35 | 5 |
| 14 | 0.5 | 0.2 | 1/2 | 70 | 30 | 9 |
| 15 | 0.5 | 0.1 | 1/3 | 75 | 25 | 9 |
| 16 | 0.1 | 1 | 5/1 | 55 | 45 | 4 |
| 17 | 0.1 | 0.5 | 2/1 | 60 | 40 | 4 |
| 18 | 0.1 | 0.25 | 1/1 | 65 | 35 | 5 |
| 19 | 0.1 | 0.2 | 1/2 | 70 | 30 | 9 |
| 20 | 0.1 | 0.1 | 1/3 | 75 | 25 | 9 |

Protocol B:

The following parameters were applied:
1. % of honey in the protocol as part of the total honey and water quantity.
2. % of water in the protocol as part of the total honey and water quantity.
3. % of coloring agents.
4. Different ratios of CBD and THC in the full profile of *cannabis* extracts.

TABLE 1B

| # | Honey % w/w | Water % w/w | Natural Coloring Agents % w/w | Cannabis Oil % w/w | CBD/THC ratio w/w | Attraction (1-10) |
|---|---|---|---|---|---|---|
| 1 | 50 | 50 | 0.10 | 1.0 | 1/9 | 4 |
| 2 | 57 | 43 | 0.10 | 1.0 | 1/9 | 5 |
| 3 | 60 | 40 | 0.10 | 1.0 | 1/4 | 6 |
| 4 | 67 | 33 | 0.10 | 1.0 | 1/4 | 9 |
| 5 | 77 | 23 | 0.10 | 1.0 | 1/4 | 8 |

The data in Tables 1A-B above suggests that according to a specific embodiment of the invention:

Honey % should be higher than 65% (e.g., 70% or more);
Water % should be lower than 35%.
4-5 are good attraction parameters.

According to another specific embodiment of the invention:
Honey % should be higher than 50% (e.g., 70% or more);
Water % should be lower than 50%.

Example 2

Cannabis Honey Production

Cannabis honey and cannabis honey with Naringin were produced using the feeding protocols.

TABLE 2A

| | in the oil | | | in the honey | | |
|---|---|---|---|---|---|---|
| Cannabis oil % | Naringin % | CBD % | THC % | CBD ppm | THC ppm | Naringin ppm |
| 0.2 | 0 | 2.7 | 1.6 | 31 | 17 | 0 |
| 0.2 | 0.5 | 2.7 | 1.6 | 30 | 17 | 5 |
| 0.2 | 0 | 10 | 5 | 95 | 52 | 0 |
| 0.2 | 0.5 | 10 | 5 | 98 | 49 | 5 |

In all preparations the level of cannabinol was less than 10 ppm.
ppm=mg/kg

An exemplary feeding protocol was used to produce Cannabis oil honey with and without Naringin.

Gas chromatography was used to detect the content of the CBD, THC and Naringin in the honey.

The data was expressed in mg/kg=ppm.

The total dilution done by the preparation of the feeding protocol and the honey bees was 1/100,000 and therefore these concentrations in the honey were expected.

Cannabis honey with the natural coloring agents was produced using the feeding protocols.

TABLE 2B

| | % Cannabis | % in the Oil | | ppm in the Bee Feed | | ppm in the Honey | |
|---|---|---|---|---|---|---|---|
| Type | Oil | CBD | THC | CBD | THC | CBD | THC |
| A | 1 | 1.3 | 13 | 103 | 381 | 8.3 | 60.14 |
| B | 1 | 2.5 | 10 | 25 | 254 | 6.0 | 51.0 |

An exemplary feeding protocol was used to produce Cannabis oil with honey.

Liquid chromatography was used to detect the content of the CBD and THC in the honey.

Example 3

Impact Evaluation on Subjects Suffering from Chronic Pain

Protocol synopsis is presented in Table 3 below.

TABLE 3

| | |
|---|---|
| Diagnosis and main eligibility criteria: | Patients in the Pain Policlinic in HaEmek MC, Israel. Patients with the chronic pain that used cannabis in the past. |
| Statistical methods: | All measured variables and derived parameters are listed individually and, if appropriate, tabulated by descriptive statistics. For descriptive statistics, summary |

TABLE 3-continued

| | |
|---|---|
| | tables are provided giving sample size, absolute and relative frequency by study group, and sample size, arithmetic mean, standard deviation, coefficient of variation (if appropriate), median, minimum and maximum, percentiles, p values, and 95% CI (Confidence Interval) by study group for means of continuous variables. Chi-square test or Fisher's Exact test (as appropriate) is applied for testing the statistical significance of the difference in percent of subjects reporting adverse events between the study groups. Paired t-test or Signed-Rank test (as appropriate) is applied for testing the statistical significance of the changes from baseline in laboratory results within each study group. ANOVA model is applied for testing the statistical significance of the difference in the changes in laboratory results between the study groups. Dunnett's method is used for comparing each of the active groups to the Placebo group. ANOVA model is applied for testing the statistical significance of the difference in immunological markers and the secondary endpoint parameters between the study groups. Dunnett's method is used for comparing each of the active groups to the Placebo group. Changes in immunological markers and efficacy parameters may be assessed across each individual subject. |

Specifically:

Each patient filled a Brief Pain Inventory (BPI) questioner (questioner #1) immediately prior to treating with smoking cannabis, 24 hours after the patients were provided with BPI questioner #2, 3 days later patients were provided with questioner #3 and immediately after treated with cannabis honey, 24 hours later patients were provided with BPI questioner #4. All together 7 patients were engaged with the study. 4 patients were diagnosed with fibromyalgia, 3 with posttraumatic stress disorder (PTSD).

The questioners were collected and the data was analyzed by t-test for each administration (cannabis and cannabis honey).

Dosing:

Active dose in cannabis cigarette—THC—16-24% PPM and CBD—2% (each patient received a cigarette of 0.8-1 gr).

Active dose in cannabis honey—THC—45 PPM and CBD—4 PPM (each patient was treated with a teaspoon of honey: 7 gr).

The analysis of the administration of cannabis honey resulted in positive trends and statistically significant changes in two indications—fibromyalgia and PTSD. The results are shown in FIGS. 2-10.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a medical condition selected from the group consisting of nausea and pain associated with cancer and chemotherapy; nausea, pain and wasting associated with AIDS; arthritis and rheumatism; glaucoma; migraine; muscle spasticity associated with multiple sclerosis and paralysis; alcohol and narcotics withdrawal; stress; depression; asthma; epileptic seizures, dementia, fibromyalgia, insomnia and post-traumatic stress disorder (PTSD), the method comprising administering to a subject in need thereof a therapeutically effective amount of pure honey comprising 5 ppm-300 ppm of one or both of tetrahydrocannabinol (THC) and cannabidiol (CBD), the pure honey being substantially free of cellulose, thereby treating the medical condition.

* * * * *